United States Patent [19]

Metcoff

[11] Patent Number: 4,818,516

[45] Date of Patent: Apr. 4, 1989

[54] METHOD OF NUTRITIONAL ASSESSMENT AND THERAPY

[75] Inventor: Jack Metcoff, Oklahoma City, Okla.

[73] Assignee: The Board of Regents for the University of Oklahoma, Norman, Okla.

[21] Appl. No.: 725,419

[22] Filed: Apr. 22, 1985

[51] Int. Cl.$^4$ .................. A61K 49/00; A61K 31/40; A61K 31/195

[52] U.S. Cl. ........................... 424/9; 514/419; 514/561

[58] Field of Search ................ 424/9; 514/419, 561

[56] References Cited

U.S. PATENT DOCUMENTS 4,279,917 7/1981 Takami et al. ................. 514/400

OTHER PUBLICATIONS

W. Beck and W. Valentine, "The Aerobic Carbohydrate Metabolism of Leukocytes in Health & Leukemia, I. Glycolysis and Respiration", Cancer Res., 12:818-822, (1952).

W. Beck and W. Valentine, "The Aerobic Carbohydrate Metabolism of Leukocytes in Health & Leukemia, II. The Effect of Various Substrates & Coenzymes on Glycolysis and Respiration", Cancer Res., 12:823-828, (1952).

T. Bucher and G. Pfleiderer, "Pyruvate Kinase from Muscle", *Methods in Enzymology*, S. P. Colowick & N. O. Kaplan, eds., Acad. Press, N.Y., 1:435-440, (1955).

B. Horecker and P. Smyrniotis, "Glucose-6-Phosphate Dehydrogenase", *Methods in Enzymology*, S. Colowick and N. Kaplan, eds., Acad. Press, N.Y., 1:323-327, (1955).

W. Beck, "The Control of Leukocyte Glycolysis", *J. Biol. Chem.*, 232:251-270, (1958).

W. Beck, "Occurrence and Control of the Phosphogluconate Oxidation Pathway in Normal and Leukemic Leukocytes", J. Biol. Chem., 232:271-283, (1958).

E. Noble et al., "Carbohydrate Metabolism in the Leukocytes, I. The Pathway of 2- and 3-Carbon Compounds in the Rabbit Polymorphonuclear Leukocyte", *J. Biol. Chem.*, 235:1261-1264, (1960).

A. Vanotti, "Metabolic Pattern of Leukocytes Within the Circulation and Outside It", *Biol. Activity of the Leukocyte,* Ciba Found. Study Grp. #10, Boston, Mass., Little Brown Publ., 79-85, (1961).

J. Frei et al., "Enzymatic Studies in the Different Types of Normal and Leukemic Human White Cells", Blood, 18:317-327, (1961).

L. Rosenberg and S. Downing, "Transport of Neutral and Dibasic Amino Acids by Human Leukocytes: Absence of Defect in Cystinuria", *J. Clin. Invest.,* 44:1382-1393, (1965).

F. Weber et al., "Insulin: Inducer of Pyruvate Kinase", Science, 149:65-67, (1965).

K. Giles and A. Myers, "An Improved Diphenylamine Method for the Estimation of Deoxyribonucleic Acid", Nature, 206:93, (1965).

J. Campos et al., "Kinetic Differences Between Human Red Cell and Leukocyte Pyruvate Kinase", Nature, 208:194-195, (1965).

H. Krebs and L. Eggleston, "The Role of Pyruvate Kinase in the Regulation of Gluconeogenesis", Biochem. J., 94:3c-4c, (1965).

R. Selvaraj and A. Sbarra, "Relationship of Glycolytic and Oxidative Metab. to Particle Entry and Dest. in Phagocytosing Cells", Nature, 211:1272-1276, (1966).

T. Yoshida et al., "Intermediary Metabolites and Adenine Nucleotides in Leukocytes of Children with Protein-Calorie Malnutrition", Nature, 214:525-526, (1967).

S. Minakami, "Studies on Leukocyte Metab., I. Glycolytic Intermed. and Nucleotides in Guinea Pig Exudate Granulocytes", J. Biochem., 63:83-88, (1968).

D. Rhoads and J. Lowenstein, "Initial Velocity and Equil. Kinetics of Myokinase", J. Biol. Chem., 243:3963-3972, (1968).

A. Boyum, "Isolation of Leukocytes from Human Blood Further Observations", Scand. J. Clin. Lab. Invest., 21:31-50, (1968).

A. Boyum, "A One-Stage Proced. for Insolation of Granulocytes and Lymphocytes from Human Blood", Scand., J. Clin. Lab. Invest., 21:51-76, (1968).

P. Leung et al., "Effect of Amino Acid Imbal. on Plasma and Tissue Free Amino Acids in the Rat", J. Nutr., 96:303-318, (1968).

J. Baierlein and J. Foster, "Studies on the Energy Metab. of Human Leuko., II. Mech. of the Pasteur Effect in Human Leukocytes", Blood, 32:412-422, (1968).

T. Yoshida et al., "Reduced Pyruvic Kinase Activity, Altered Growth Patterns of ATP in Leuko. and Protein-Calorie Malnutr.", Am. J. Clin. Nutr., 21:162-166, (1968).

D. Atkinson, "The Energy Charge of the Adenylate Pool as a Regulatory Parameter. Interaction with Feedback Modifiers", Biochem., 7:4030-4034, (1968).

R. Gallo and S. Perry, "The Enzymatic Mech. for Deoxythymdine Syn. in Human Leu., IV. Compar. Between Norm. & Leukemic Leukocytes", J. Clin. Inv., 48:105-116, (1969).

(List continued on next page.)

Primary Examiner—John W. Rollins
Attorney, Agent, or Firm—Dunlap, Codding & Peterson

[57] ABSTRACT

A method for assessing nutritional status and treating a nutritional disorder in a subject. The subject's intracellular status is monitored by measuring selected intracellular amino acids and at least one intracellular metabolic process. Primary intracellular amino acids are identified for the metabolic process and the level of each is compared to normal. Treatment includes administration of a composition comprising the normal plasma concentrations of certain secondary amino acids identified for each of the abnormal primary amino acids. The cellular assessment is preferably performed on leukocytes obtained from a blood sample.

34 Claims, No Drawings

OTHER PUBLICATIONS

T. Yoshida et al., "Human Fetal Growth Retard., II. Energy Metab. in Leukocytes", Pediatrics, 50:559–567, (1972).

K. Winkler, "Kinetics of the Flow of Amino Acids from the Extracell. Space and the Intracellular Pools Resulting in Protein Synthesis", *Hoppe-Seyler's Z. Physi. Chem.*, 353:782–786, (1972).

J. Van Berkel and J. Koster, "M-Type Pyruvate Kinase of Leukocytes: an Allosteric Enzyme", Biochem. Biophys. Acta, 293:134–139, (1973).

J. Metcoff et al., "Energy Metab. and Prot. Syn. in Human Leuko. During Pregnancy and in Placenta Related to Fetal Growth", Ped., 51:866–877, (1973).

J. Patrick and P. Hilton, "The Response of the Hum. Leukocyte to Alterations in Extracell. Osmolality", Clin. Sci., 44:456–465, (1973).

P. Hilton and J. Patrick, "Sodium and Potass. Flux Rates in Normal Hum. Leuko. in an Artificial Extracell. Fluid", Clin. Sci., 44:439–445, (1973).

L. DeChatelet et al., "Inhibition of Amino Acid Inc. into Protein of Hum. Neutrophils by Phagocytosis", Infection & Immun., 8:791–796, (1973).

J. Van Berkel, "Some Kinetic Properties of $M_2$-Type Pyruvate Kinase from Rat Liver at Physiol. $Mg^{2+}$ Concen.", Biochimica et Biophys. Acta, 370:140–152, (1974).

J. Metcoff, "Biochem. Markers of Intrauterine Malnutr.", *Nutr. and Fetal Devel.*, M. Winick, ed., J. Wiley & Sons, publ., pp. 24–44, (1974).

J. Metcoff, "Enzymatic Indices of Fetal Malnutr.", *Mod. Prob. in Ped.*, vol. 14, F. Falkner et al., eds., S. Karger, publ., 57–67, (1975).

J. Metcoff, "Cellular Energy Metab. in Protein-Calorie Malnutr.", *Protein-Calorie Malnutrition*, Acad. Press, 65–85, (1975).

M. Mameesh et al., "Kinetic Prop. of Pyruvate Kinase in Hum. Maternal Leukocytes in Fetal Malnutr.", Pediat. Res., 10:561–565, (1976).

Y. Houpert et al., "Comparison of Proced. for Extracting Free Amino Acids from Polymorphonucl. Leukocytes", Clin. Chem., 22:1618–1622, (1976).

F. Shinnick and A. Harper, "Effects of Branched-Chain Amino Acid Antag. in the Rat on Tiss. Amino Acid and Keo Acid Concen.", J. Nutr., 107:887–895, (1977).

J. Metcoff, "Relation. of Leuko. Metab. to Maternal Nutr. Status & Fetal Growth", Malnutr. & the Immune Response, R. Suskind, ed., Raven Press, N.Y., 285–292, (1977).

"Leukocyte Transketolase Activity: an Indicator of Thiamin Nutriture", *Nutrition Reviews*, 35:185–187, (1977).

W. Crosby et al., "Fetal Malnutr.: an Appraisal of Correlated Factors", Am. J. Obst. and Gynec., 128:22–31, (1977).

J. Patrick & M. Golden, "Leukocyte Electrolytes and Sod. Transport in Protein Energy Malnutr.", Am. J. Clin. Nutr., 30:1478–1481, (1977).

P. McClain et al., "Relation. of Maternal Amino Acid Profiles at 25 Wks. of Gestation to Fetal Growth", Am. J. Clin. Nutr., 31:401–407, (1978).

J. Metcoff et al., "Cell Metabolism in Uremia", *Am. J. Clin. Nutr.*, 31:1627–1634, (1978).

D. Baron and G. Levin, "Intracellular Chemical Pathology", *Recent Advances in Clinical Biochem.*, Churchill Livingston, N.Y., 1:153–174, (1978).

J. Ghisolfi et al., "Plasma Free Amino Acids in Normal Children and in Patients with Proteinocaloric Malnutr: Fasting & Infections", Ped. Res., 12:912–917, (1978).

J. Tews et al., "Induction of Threonine Imbal. by Dispensable Amino Acids: Relation to Competition for Amino Acid Trans. into Brain", 109:304–315, (1978).

F. Wells and B. Smits, "Leukocyte Amino Acid Concen. & Their Relation. to Changes in Plasma Amino Acids", J. Par. & Ent. Nutr., 4:264–267, (1980).

J. Metcoff, "Maternal Nutrition and Fetal Development", *Early Human Development*, 4:99–120, Elsevier/N.-Holland Biomed. Press, (1980).

J. Metcoff et al., "Maternal Nutrition and Fetal Outcome", *Am. J. Clin. Nutr.*, 34:708–721, (1981).

D. Rannels et al., "The Measurement of Protein Synthesis in Biological Systems", Life Sciences, 30:1679–1690, (1982).

K. Fukuda, T. Usui, "Char. Patterns of Free Amino Acid Content in Plasma, Erythrocytes, Lympho., & Granulo. in Man", Kiroshima J. Med. Sci., 32:163–166, (1983).

J. Metcoff et al., "Effects of Amino Acid Infus. on Cell Metab. in Hemodialyzed Patients with Uremia", Kidney Internat., 24:S-87–S-92, (1983).

J. Patrick and C. Dervish, "Leukocyte Zinc in the Assessment of Zinc Status", *CRC Crit. Rev. Clin. Lab. Sci.*, 20:95–114, (1984).

D. Baron & S. Ahmed, "Intracell. Concen. of Water and of the Prin. Electrolytes Determined by Anal. of Isolated Human Leukocytes", Clin. Sci., 37:205–219, (1969).

M. Brenner et al., "Control of Aminoacyl Transfer Ribonucleic Acid Synthetases", J. Biol. Chem., 245:450–452, (1970).

R. Baehner et al., "Respiration and Glucose Oxidation in Human and Guinea Pig Leukocytes: Comp. Studies", J. Clin. Invest., 49:692–700, (1970).

J. Metcoff et al., "Biomolecular Studies of Fetal Malnutrition in Maternal Leukocytes", Pediatrics, 47:180–191, (1971).

M. Jemelin & J. Frei, "Metabolisme Energetique du Leukocyte", *Ann. Biol. Clin.*, 29:109–111, (1971).

K. Winkler et al., "Proteinsynthese in Menschlichen Leukocytes", *Klin. Wschr.*, 49:225–227, (1971).

METHOD OF NUTRITIONAL ASSESSMENT AND THERAPY

FIELD OF THE INVENTION

The present invention relates generally to methods of assessing and treating nutritional disorders in subjects.

SUMMARY OF THE INVENTION

The present invention is directed to a method for assessing nutritional status in a subject. The rate of a selected intracellular metabolic process and the intracellular levels of selected amino acids are measured. Primary intracellular amino acids are identified for the metabolic process that is measured, and the primary amino acids which are present at abnormal levels are identified.

The present invention is further directed to a method for treating a subject for a nutritional disorder. The rate of a selected intracellular metabolic process and the intracellular levels of selected amino acids are measured. Primary intracellular amino acids are identified for the metabolic process that is measured, and the primary amino acids which are present at abnormal levels are identified. For each of the primary amino acids present at an abnormal level, a set of secondary extracellular amino acids is identified. Then an effective amount of a nutrient composition comprising the normal extracellular concentrations of the secondary amino acids identified for each abnormal primary amino acid is administered to the subject.

Still further, the present invention is directed to a method for treating a subject for a nutritional disorder wherein a nutrient composition is administered to the subject in an effective amount, and wherein the nutrient composition comprises the normal extracellular concentrations of secondary amino acids selected as previously described.

DESCRIPTION OF THE PREFERRED EMBODIMENT

Nutritional status is a function of intracellular metabolic processes which synthesize proteins, fats and carbohydrates and generate energy from nutrients which enter the cell from the surrounding body fluids and tissues. These continuous and dynamic metabolic processes are mediated by various enzyme systems. If the enzyme systems are intact, the success of the metabolic processes depend on the quality, quantity and balance within the cell of the nutrients, such as amino acids, electrolytes, trace minerals and glucose.

The diagnosis and treatment of nutritional disorders, such as malnutrition and Kwashiorkor, traditionally have been based primarily on visual examination and fat fold and upper arm circumference measurements. Plasma levels of nutrients also have been analyzed. Acute nutritional disorders have been treated by intravenous administration of solutions comprising a broad spectrum of nutrients, a so called "shot gun" approach.

The present invention is directed to a method for accurately assessing the nutritional status of a subject by measurement of intracellular nutrient levels and analysis of metabolic processes. Based on data obtained from a population of study subjects, a subset of intracellular nutrients which normally accounts for a relatively large and significant proportion of the variance in the selected nutrient-dependent metabolic process, such as protein synthesis, is identified. The nutrients which make up this subset are referred to as primary nutrients.

Likewise, by analyzing concurrent plasma levels of nutrients in conjunction with such intracellular measurements in a population of study subjects, a subset of plasma nutrients may be identified which normally account for levels of primary nutrients within the cells. Thus, these plasma nutrients, called secondary nutrients, indirectly improve the function of the intracellular metabolic processes. By administering to the subject having a nutritional disorder, a nutrient composition comprising a combination of secondary nutrients selected in response to the subject's intracellular levels of primary nutrients, the nutritional disorder may be treated.

As metabolic processes occur in all nucleated cells, nucleated cells from any body tissue are suitable for measuring intracellular nutrients and metabolic activities. Leukocytes are preferred cells for these measurements as leukocytes are readily accessible, have relatively short half-lives in circulation, are rapidly reproduced, and have a high rate of protein synthesis in relation to protein degradation.

The procedures described below are adapted for leukocytes. It is to be understood that where cells of other body tissues are selected to be measured, the procedures should be modified accordingly. For example, where muscle cells are selected, such cells may be obtained by needle biopsy instead of venous blood sampling which is the preferred method for obtaining blood cells, such as leukocytes.

Obtaining a Cell Sample

In accordance with the method of the present invention, cells of the type selected for measurement of the subject's nutrients and metabolic activity, are obtained. Where leukocytes are selected, a venous blood sample, preferably in an amount of 2.5 ml to 3 ml, is obtained, and placed in a vessel in combination with a heparin-dextran preparation ("hep-dex"). Preferably, the blood sample is withdrawn from the subject by venapuncture using a heparinized syringe and then transferred to the vessel. If such a procedure is followed, the needle preferably is removed from the syringe before the blood is expressed into the vessel. A preferred vessel is a blood collection tube, such as a red stoppered Vacutainer No. 6432 (125 mm length) or a red stoppered Veniject No. KT-200 (100 mm length).

The hep-dex solution preferably comprises about one million units of sodium heparin (Sigma, No. H3123), about 15 grams of dextran having an average molucular weight of 81,600 (Sigma, D4751), and about 1.27 grams of sodium chloride, in sterile water in an amount sufficient to bring the total volume of solution equal to 250 ml. The solution, which is preferably placed in the vessel before the blood, is combined with the blood in a ratio of about 1 ml of hep-dex solution to about 8 ml of blood.

Having placed the hep-dex solution and the blood sample in the vessel, the vessel is then covered, such as by sealing with a parafilm cap. The contents of the vessel are then gently mixed, such as by manually inverting the vessel about three times. The total volume of fluid in the vessel preferably is measured and recorded.

The vessel then preferably is maintained at 4° C. for thirty minutes to allow the blood/hep-dex mixture to settle. For example, the vessel, such as the tube, may be immersed in a larger vessel, such as a beaker, containing crushed ice. In order to facilitate settling and to maximize the surface of the plasma-cell interface, the vessel preferably is tilted at about a 45° angle while settling and preferably is immersed to a depth so that the level of the ice is above the meniscus of the mixture in the tilted vessel.

Separation of Plasma and Granulocytes

After the blood/hep-dex mixture has settled, the plasma and the leukocytes are each separated for testing. The separation procedures described herein are carried out under cold ambient temperatures (4° C.). A preferred method of separation is centrifugation. If centrifugation is used for separation, the plasma first is gently removed from the vessel preferably by silonized glass pipettes and carefully layered over a gradient medium in a centrifuge tube. A preferred centrifuge tube is a 1.5 ml polystyrene tube with cap (Corning No. 25310). A preferred gradient medium is a Ficoll solution which is a mixture of Ficoll 400 (a polysaccharide) and sodium diatrizoate, adjusted to a density of 1.077. Suitable Ficoll solutions include Ficoll-Hypaque (Pharmacia) and Sigma No. 1077. In transferring the plasma to the centrifuge tube, great care should be exercised not to allow the plasma to break the interface between the plasma being added and the Ficoll solution, so as to keep the cells which are contained within the plasma, above the Ficoll solution.

The centrifuge tubes containing the plasma and Ficol solution preferably are gently centrifuged in the cold (4° C.) until the cell layers are well defined. Centrifuging for about 25 minutes at about 250 × g is preferred. It is to be understood that unbalanced centrifuging may cause the cell bands to scatter and be undefined.

After centrifugation, the components of the blood/hep-dex mixture will be disposed in well-defined layers as follows: plasma (uppermost in the tube); a white layer comprising lymphocytes; a clear layer comprising Ficol solution; and granulocytes and erythrocytes pelleted at the bottom of the tube. Each of these layers, except the granulocyte/erythrocyte pellet, is removed one at a time and working from top to bottom, preferably by using a silonized pipette (Pasteur).

The plasma preferably is transferred to a vessel, such as a blood collection tube, which tube is kept cool (4° C.) such as by placing it in crushed ice. The Ficoll solution and the lymphocytes may be discarded.

The granulocytes next are isolated by lysing and removing the erythrocytes. The erythrocytes and granulocytes pelleted at the bottom of the tube preferably are resuspended in about 2 ml to about 3 ml of a salt solution comprising isotonic combinations of potassium chloride,and sodium chloride in water. A preferred salt solution is Hank's Balanced Salt Solution having a pH of about 7.0 and comprising reagent grade water, CAP type II or better, 3.5 percent sodium chloride (w/v) solution and 0.16M potassium chloride.

The suspension of erythrocytes and granulocytes may then be transferred using a siliconized pipette (Pasteur) to a conical centrifuge tube which preferably is larger than the tube used to centrifuge the entire sample as described above. A preferred centrifuge tube for the erythrocyte/granulocyte suspension is a 50 ml polypropylene centrifuge tube (Nalgene No. 3103). To assure that substantially all the erythrocytes and granulocytes have been removed from the small tube, another 2 ml to 3 ml salt solution, such as Hank's solution, may be used to rinse the tube and then transferred to the larger conical centrifuge tube.

Additional salt solution, such as Hank's solution, is placed in the conical centrifuge tube to bring the total volume to about 15 ml. The 15 ml mixture should be visually inspected for fibrin clumps. If any are observed, these preferably are removed by aspiration with a siliconized pipette, if possible. The cells in the salt solution preferably are gently centrifuged with balance for about 5 minutes at about 250 × g. The supernatant then is removed by decanting.

The granulocytes and erythrocytes remaining in the tube after removal of the supernatant are resuspended in a solution comprising about 5 ml of a salt solution, as described above, such as Hank's solution, and about 15 ml of distilled water to lyse the erythrocytes. This suspension then is mixed gently at lowest speed on Vortex for exactly thirty seconds. After the thirty second mixing, the solution is immediately returned to isotonicity by adding about 5 ml of 3.5 percent sodium chloride solution. The isotonic suspension then is gently mixed again, and centrifuged again with balance for about 5 minutes at about 250 × g. The supernatant then is removed, as by decanting, and discarded.

The pellet of cells remaining after the lysis procedure, comprising substantially all granulocytes, preferably is washed again. The cells may be resuspended in about 15 ml of isotonic salt solution, such as Hank's solution, and gently centrifuged with balance at about 250 × g for about 5 minutes. The supernatant is removed, such as by decanting it out of the tube. The pellet of cells will remain adhered to the bottom of the centrifuge tube. The centrifuge tube is inverted and allowed to drain for about one minute.

The pellet of cells next preferably is resuspended in about 0.5 ml of 0.16M potassium chloride. This suspension of granulocytes is in condition for dilution and analysis. It should be noted that the separation and preparation of granulocytes should be completed within about two hours from the time the venous blood sample was obtained from the patient. At all times the cells must be handled gently and should be maintained under cool conditions, preferably at 4° C., such as on ice or in a cold (4° C.) room, to maintain cell viability.

The percentage of the granulocytes may be counted automatically, as by a Coulter counter, or manually by direct microscopic visualization of a hemocytometer containing the appropriate dilution of cells. To determine whether the cells are viable, about 1 drop (50 $\mu$l) of a vital dye, preferably Trypan blue 0.5%, is added to the suspension on the hemocytometer. One hundred cells are counted. The viable cells do not allow the dye to enter. Cells which are not viable take up the dye. When the isolation procedure is satisfactory about 95% to 97% of the granulocytes will be viable and will exclude the dye.

Dilution of Granulocyte Preparation

The preparation of concentrated granulocytes preferably is diluted in 0.16M potassium chloride to a concentration which is suitable for analysis. The concentration is measured by optical density. An absorbance of 340 nm preferably is used as a reference. A preferred final solution reads about 0.30 to about 0.50, at $A_{340}$ of a 1:21 dilution.

The concentrated granulocyte suspension preferably is diluted by adding small amounts of the potassium chloride solution in increments until the desired concentration is obtained. For example, about 10 μl of the concentrated granulocyte suspension may be added to a vessel, such as a cuvet containing about 200 μl of the potassium chloride solution. The mixture may be then stirred with a plastic stirring stick and the optical density measured.

If the optical density indicates that the mixture is still too concentrated, additional potassium chloride solution may be added and the optical density measured again.

As regards optical density measurement, it is preferable to take each measurement at least twice. A third reading should be taken if the first two readings differ by more than five percent. In any event, each optical density measurement should be recorded.

It should be noted that the granulocytes settle out of suspension relatively rapidly. For this reason, the concentrated granulocyte suspension should be gently agitated to remix the suspension prior to taking any sample or aliquot from it. At all times the suspensions of granulocytes, diluted and concentrated, should be handled gently and kept at about 4° C. (on ice) whenever possible.

Measurement of Intracellular and Extracellular Water

The intracellular and extracellular water content of the isolated granulocytes preferably is measured. A measured volume, preferably less than 0.1 ml, of the diluted granulocyte suspension, prepared as described above, preferably is placed in a clean, dry and pre-weighed microcentrifuge tube, such as a 1 ml polyethylene microcentrifuge tube (Fisher No. 05-407-5). The granulocytes are packed, preferably by gentle centrifugation for about 5 minutes at about 200 × g. The supernatant is then removed and the microcentrifuge tube is turned upside down and allowed to drain on filter paper for about one minute.

To obtain an accurate weight of the granulocytes, excess moisture preferably is removed from the microcentrifuge tube such as by using a lint-free wiper to wipe the inside of the tube. The tube containing the granulocyte is then weighed, preferably on a microanalytical balance readable to 0.01 mg (Mettler), to obtain a "wet" weight. To ensure an accurate weight the tube should be handled using dry, plastic gloves or forceps. The granulocytes are then resuspended, preferably in a tris-citrate solution, such as 0.1M tris-citrate, pH 7., in a volume equal to the measured amount, less 10 μl of diluted granulocyte suspension placed in the microcentrifuge tube prior to obtaining the wet weight.

Radio isotope-labeled inulin, about 10 μl, is added to the granulocyte-tris-citrate solution which is mixed gently. A suitable inulin for this purpose is $^{14}C$ inulin at a concentration of 11 mg/ml in 0.1M tris-citrate, pH 7.4, so that it contains 0.25 Ci/10 μl. The mixture is centrifuged gently at about 200 × g for about 5 minutes. The supernatant is removed and the tube weighed as before.

Next the granulocyte pellet is freed, as by adding a small amount of the tris solution. The free granulocytes are then transferred to a pre-weighed paper filter, such as a Whatman GF/A 2.4 cm filter. The filter containing the granulocytes is transferred, preferably using forceps, to an oven having an adjustable temperature for drying. The filter is heated in the oven for about one to about two hours at about 75° C. Again using forceps, the filter with the dried cells is cooled to ambient temperature in a dessicator, weighed on a balance as before and the dry weight recorded.

After the dry weight is measured, the dried filter containing the cells is placed in a scintillation vial. A scintillator fluid "cocktail" comprising 0.4% PPO (2.5 diphenyloxazole) 0.01% POPOP (1.4 bis [2-(5-phenyloxazolyl)]benzene)in toluene, in weight for volume of toluene, is next added to the vial and placed in a scintillation counter and counted three times at five minute intervals in the dissociations per minute (DPM) mode.

It should be noted that it is necessary to know the number of DPM's added to the 10 μl suspension containing the labeled inulin solution. This may be determined for a single batch separately by pipeting 10 μl of the $^{14}C$ inulin solution directly onto a filter, drying and counting as above. The known value of the activity of a single batch may then be used in subsequent scintillation counts using the same labeled inulin solution.

The extracellular water content may be calculated using the following equations:

Wet weight(A) = Wt. of tube + cells − Wt. of tube.

Dry weight(B) = Wt. of filter + dried cells − Wt. of filter.

Water weight(C) = A − B.

$$\text{Extracellular water}(ECW) = \frac{DPMs \text{ of dried cells}}{DPMs/10 \ \mu l} \times C$$

Intracellular water (ICW) = C − ECW.

$$\text{Percent of } ICW = \frac{ICW}{A - ECW} \times 100$$

The theory of using radioactive inulin to calculate ECW is based on the observation that inulin, a high molecular weight starch, is not metabolized, and does not bind to, or cross, the cell membrane, but instead remains in the extracellular fluid, not otherwise affecting cell structure or viability. As the cells are pelleted by centrifugation, a certain amount of the suspending solution is trapped between the cells. Using higher g's to pack the cells tighter causes marked damage, so lower forces become the desired alternative. The radioactivity remaining in the cell pellet gives a good estimation of the "trapped" ECW present.

Measurement of Protein Synthesis

The pre-treatment rate of protein synthesis in the subject preferably is measured by determining the rate at which the isolated cells incorporate radioactively labeled amino acid into newly synthesized proteins. This measurement should be taken as soon as possible after the cells are isolated. First, about six stop tubes containing about 1 ml of 10% Trichloracetic acid (TCA) are chilled on ice. Next, a reaction mix is prepared and preincubated to about 37° C. in a shaker incubation bath.

The reaction mix comprises 100 ml q's 0.14M sodium chloride; 25 ml 0.1M tris-hydrochloric acid, pH 7.5, in 0.14M sodium chloride; 0.50 ml 0.1M magnesium chloride; 0.20 g glucose (dextrose); 0.05 ml MEM with Earl salts and 10 percent fetal bovine serum, such as MEM composition, may be obtained from Gibco, No. 320-1112. To each bottle of MEM is added 15 mg glutamine, 5000 units penicillin, 0.5 mg streptomycin and 10 mg kanamycin.

The reaction mix is fitered using about 0.2 micron poresize filters. The filtered mix is transferred in aliquots of about 2 ml to 3 ml to sterile polystyrene tubes, capped and irradiated with an ultraviolet light for about 30 minutes. The irradiated mix is frozen.

About 50 μl of the diluted cell suspension, prepared as above, is added to each preincubated tube containing the reaction mix and vortexed gently. The time at which the cell suspension is added is noted. The tubes containing the cell suspension are incubted at about 37° C. in a shaker bath. 30 μl of the cell-containing reaction mix in each tube is removed by pipette from the tube at 10, 20 and 30 minute time periods and transferred to the chilled stop tubes, noting the exact time of each transfer. A blank tube is prepared as a control by adding 24.2 μl of reaction mix and 5.8 μl of diluted cell suspension to an empty stop tube, incubating it for 30 minutes and processing it in the same manner as the other six stop tubes. The control tube and the six sample tubes are stored on ice until ready for further processing, but in no event for more than five hours.

The cells from each of the sample-containing stop tubes is filtered. A suitable ten-place filter apparatus with holders, or grids, for 24 mm diameter filters may be obtained from Hoeffer Scientific Instruments (San Francisco, Calif.). Other sizes of filter apparatuses may be obtained from Millipore. A GF/A glass microfibre filter, preferably a 2.4 mm diameter filter (Whatman Co. through Scientific Products Co.), is placed on each of six filter holders on the filter apparatus. The filters are then moistened with a small amount of a wash solution comprising 50 mg l-leucine per 100 ml of five percent TCA. Vacuum is next applied and each filter is inspected for holes. Faulty filters are replaced, each replacement filter being wetted and inspected.

The sample-containing stop tubes are vigorously vortexed and the sample from each tube is then poured on one of the six filters. The time at which each sample is placed in the stop tube is the stop time of the sample. Each tube is rinsed twice with 2-3 ml of the 5% TCA/-leucine wash solution, and the rinse also poured through its respective filter, to assure that substantially all the cells from each sample have been deposited on the filter. The filters are each rinsed two more times with the 5% TCA/leucine wash solution, 4-5 ml being dispensed to each filter at a time from a squirt bottle. The filters are each given a final wash with 95% ethanol.

The cell-containing filters are allowed to air dry for a few minutes, preferably using vacuum to accelerate drying. Using forceps, each of the dried filters is placed in a scintillation vial and oven dried at about 75° C. for about 30 minutes. The scintillation vials are then removed from the oven and cooled in a dessicator. To each vial 10 ml of scintillation solution, comprising 0.4% PPO and 0.01% POPOP in toluene (w/v), is added.

The uptake of leucine is measured in picomoles (pmoles) of leucine per hour per ml Of the original granulocyte suspension. About 10 ml of a leucine solution first is prepared which comprises about 1.0 ml 89 μM leucine in sterile saline. The final activity of this solution preferably comprises 10 μl-1 Ci=1000 pmoles leucine. This solution preferably is kept refrigerated.

The undiluted MEM solution, described above, comprises 52.4 mg leucine per liter. A one percent dilution of this MEM solution would thus provide 400 pmoles of leucine per 100 μl of diluted MEM. When 100 μl of the diluted MEM solution is combined with the 10 μl of the 3H-leucine solution prepared as bbove, an assay solution comprising a total of 1400 pmoles results.

The DPM's of the assay solution is next determined using a 10 μl "spot" of a 1:100 dilution of the assay solution on a GF/A filter and the filtration and counting methods and equipment described above for counting incorporation of the isotope by the cells. The counting methods then used to calculate the DPM are preferably those provided in the instruction manual for the counter being used. Often this will be Channels ratio. It should be noted that presently available instruments will provide a filter counting efficiency of about 50 percent.

The preferred isotope, described above, according to the supplier's data comprises $1\mu Ci = 2.22 \times 10^6$ DPM. Based on this, the sample of 10 μl then which comprises 0.1μCi should equal about 220,000 DPMs. Dividing this figure into the DPM of the assay calculated as above, usually 50 percent, the efficiency of the counting on filters may be determined. The procedure described above usually yields an efficiency of about 0.7 or 70 percent.

It is believed that the 30 percent loss in efficiency is due to the geometry of the filter in the scintillation vial and is probably not due to quench. For this reason, the use of usual quench correction methods are not preferred. The calculations used to measure leucine uptake should reflect this 30 percent loss of efficiency, such as by dividing the DPM of each sample by 0.7. However, another and preferred method of accounting for the decreased efficiency is to incorporate the correction into each specific activity constant as, for example, by the following equation:

$$\frac{2.22 \times 10^6 \ DPM \ (\text{in } 1\mu \ Ci)}{1400 \ \text{pmoles (total leucine in assay)}} = \frac{1586 \ DPM}{\text{pmole}}$$

Then, efficiency loss may be accounted for by multiplying 1586 DPM/pmole by the decimal representing the calculated efficiency. For example, an efficiency of 0.701 would yield 1112 DPM/pmole. The efficiency should be taken for about 10-12 vials to determine an average value for use in the protein synthesis calculation discussed below.

It should be noted that an additional loss of efficiency may be caused by the protein precipitate trapping counts in actual assay procedures. However, as the amount Of this additional efficiency loss is believed to be negligible, this fact may be ignored in the above calculations.

The currency of the standard quench curve should be confirmed. This may be done by using the Channels ratio method. Alternatively, if the scintillation equipment being used only has the capacity to measure counts per minute (CPM), the CPM may be measured and divided by the DPM value to give the efficiency. This step may be eliminated if the scintillation counter used prints out all data in the DPM.

At least two CPM measurements are then taken of each cell sample. If the difference between the two values is greater than ten percent, the lower value preferably is used unless a filter leak is suspected. A graph may be prepared showing the cell sample CPMs plotted against elapsed time. In this way, the line should intersect the zero time ordinate between 40 CPM and 100 CPM. The change may be calculated in CPM per hour.

The calculated change for duplicate measurements preferably is averaged if the difference is less than ten percent. In consistent duplicate measurements of a sample (a difference of greater than ten percent) should be recorded. It should be noted that, in lieu of manual plotting, a linear regression formula may be used.

The equation for calculating protein synthesis by leucine uptake in the cell is as follows:

$$\frac{\frac{CPM/hr \text{ of blank}}{\text{counter eff.} \times 0.01} \times \frac{\text{total vol. of assay}}{\text{amt. removed for precipitation}} \times \frac{1,000}{\text{vol. cells used}}}{DPM/\text{pmole leucine}} =$$

pmoles leucine/hr/ml

Measurement of Plasma and Intracellular Amino Acids

The subject's pre-treatment plasma and intracellular nutrient levels are assessed. Such nutrients comprise amino acids, electrolytes, minerals, vitamins, glucose products (metabolites), enzymes and other elements required for protein synthesis and energy production to proceed normally. Preferably 19 to 35 amino acids are determined, which, if done according to the procedures described below, will take up to about four hours.

The amino acid level measurements preferably are made with a high pressure single column analyzer. A suitable analyzer is a modified Dionex D-300 Amino Acid/Peptide Analyzer with a Spectro-Physics computing integrator. The automated HPLC system preferably features post column o-phtalaldehyde (OPA) derivatization and fluorescence detection to the picomole level.

A sodium form column (Pickering No. 1193250) preferably is employed in a 25 cm stainless steel tube having an internal diameter of 3 mm. The tube may be packed with a cation exchange resin, such as DC-5A or other similar resin. Amino acids are eluted from the column preferably, by sequential application, of a series of five specially formulated buffers each at a different pH ranging from 2.2–4.9, at two column temperatures, 46° C. and 69° C. Eluent and reagent pumps preferably are calibrated to deliver reagents at flow rates of about 18 ml per hour.

Plasma (or muscle cell) samples preferably are prepared for analysis by combining 4 parts or 800 μl of plasma with 1 part or 200 μl 10 percent sulfosalicylic acid (SSA) to provide final SSA concentration of 2 percent. The mixture is then vortexed and allowed to deproteinate for about 1 hour at about 40° C. The mixture is then centrifuged at about 4000 × g for about 5 minutes and the supernatant collected. A supernatant solution is prepared by combining 11 parts (600 μl) supernatant with 1 part (54.5 μl) norleucine (NLEU), internal standard, in 1.0M sodium hydroxide. This plasma (or muscle cell) preparation may be filtered and analyzed, preferably in aliquots of about 40 μl.

To prepare leukocytes for amino acid analysis, about 400 μl of the concentrated cell suspension prepared above is frozen to about −20° C. and then thawed to ambient temperature. To the thawed concentrate about 25 μl of 10 percent SSA is added to provide a final SSA concentration of 0.6%. The mixture is then vortexed and centrifuged in the same manner as the plasma preparation above. The supernatant may then be collected, filtered and analyzed preferably in aliquots of 80 μl.

A control or standard solution is also preferably prepared. It may comprise a combination of Pierce No. 20086 and Pierce No. 20087 diluted to a concentration of 25 nm/ml with sodium citrate having a pH of 2.20. The control is anayzed in 40 μl aliquots.

Each aliquot of plasma, muscle and leukocyte preparation is diluted with a sodium citrate buffer having a pH of 2.20, to have a total volume of 100 μl. Before the sample for analysis is injected, the column is regenerated with a solution of 0.2N sodium hydroxide and 0.002N EDTA (sodium salt) for ten minutes. An eluent is next injected and reagent pumping is begun. Once the system has reached equilibrium (stable baseline), the diluted aliquot to be analyzed is injected. An initial temperature of 46° C. is used. A first buffer is used to elute phosphoserine, phosphoethanolamine, taurine, methionine sulfoxide, aspartic acid, threonine, serine and apargine (which are poorly resolved), glutamine, glutamic acid, citrulline, glycine and alanine. At the baseline following alanine, a switch is made to a second buffer in which alpha amino butyric acid and valine are eluted. The temperature of the column is then increased to 69° C. phenylalanine, B alanine, amino-isobutyric acid, ethanolamine, gamma-amino butyric acid, ammonia (as ammonium sulfate) and tryptophane. A fourth buffer is next introduced which elutes hydroxylysine, ornithine, 1-methylhistidine, lysine, histidine, 3-methylhistidine and anserine. A fifth eluent then will be used to elute the remaining amino acids, carnosine and arginine.

During the run, peak areas and retention times are automatically stored by the Spectra-Physics System 1. This information is then printed and preferably is retained for subsequent calculations. Standards preferably are analyzed for control between every four unknowns.

The subject's plasma and intracellular amino acid levels are noted and compared to known normal values. The extent the subject's amino acid levels deviate from normal is noted.

Determination of Primary Nutrients

Once the subject's intracellular nutrient levels, such as amino acid levels, have been assessed and the subject's rate of protein synthesis has been measured, it may then be determined which subset of the intracellular nutrients are primary, that is, which subgroup of, for example, the amino acids have the most substantial impact on the cell's ability to synthesize protein. Standard or normal primary nutrients may be determined by application of a covariate statistical analysis preferably carried out by computer on a population of study subjects. Each of the subject's intracellular nutrient levels is compared with the standard value for that nutrient. For example such a multivariate statistical analysis of adult subjects may reveal that of more than thirty amino acids measured, methionine, isoleucine, leucine, phenylalanine and histidine account for 54% ($R^2 = 0.54$) of the variance in the rate of protein synthesis.

It is believed that subsets of certain nutrients may be found to be standards. However the standards for primary nutrients are expected to vary according to the age, sex or physical condition of the subject. The values for the subject may deviate from one standard. The extent of deviation is noted.

Determination of Secondary Nutrients

Having determined the subject's level of primary intracellular nutrients, it is next determined which subset of plasma nutrients promotes an increase in each of the primary nutrients which deviate from one standard, thereby having a secondary or indirect effect on the level of primary nutrients.

The secondary nutrients in the standard for each primary nutrient may be identified also by use of a multivariate statistical analysis procedure which also preferably is performed by computer. For example, if it has been determined that one of a subject's primary nutrients is the amino acid leucine, appropriate statistical analysis may identify histidine, valine, citrulline and threonine as leucine's secondary nutrients; that is, the specific subset of plasma amino acids which predominately account for the intracellular level of leucine.

Verification of Efficacy of Proposed Therapy

Prior to treating the subject it is preferred to verify that administration of a nutrient composition comprising the secondary nutrients will be effective in vivo to treat the subject's nutritional disorder; that is, to result in improved function of the metabolic processes, such as protein synthesis. In vitro testing is a preferred verification method.

A nutrient composition is prepared comprising the subject's pre-determined secondary nutrients; selected in response to the subject's intracellular primary nutrient levels, in concentrations effective to improve metabolic function. It should be noted that the nutrient composition may also comprise primary nutrients so that they are available for transport into and use within the cell.

A fresh venous blood sample is obtained from the subject using the same procedure as described above. The cells, such as granulocytes, are isolated and prepared as before and incubated in the nutrient composition at 37° C. for about thirty minutes. After incubation, the rate of protein synthesis in the subject's leukocytes is measured, also as described above. If the incubated granulocytes demonstrate improved in vitro protein synthesis, as predicted, the efficacy of treating the subject with the proposed nutrient composition is verified.

Administration of Nutrient Composition

The nutrient composition is administered to the subject in an amount effective to treat the disorder. The composition may be administered intravenously or enterally. The effective amount preferably is determined by reference to parameters such as the subject's body weight and surface area, and other relevant variables including the extent of the subject's disorder. Typically, nutrient composition comprising amino acid solutions range from about 3% to about 10%, with a preferred range of about 5%. The rate of infusion preferably is adjusted so that preferably from about 0.5 grams to about 1.5 grams of amino acids per kilogram of bodyweight per day.

At intervals during and following administration of the nutrient composition, it is preferable to monitor the effect of the therapy on the subject by periodic assessment of improvement of metabolic function, such as by measuring the rate of protein synthesis. Further, periodic reassessment of the subject's intracellular and plasma nutrient levels may lead to modifications of the prescribed nutrient composition to promote enhancement of protein synthesis or other nutrient-dependent intracellular processes.

It is to be understood that measurement of other parameters of metabolic function may be useful in assessing nutritional status. These parameters include, but are not limited to, intracellular energy charge, glycolytic enzyme activity, adenine nucleotide activity, DNA values and protein levels.

EXAMPLES

1. Comparison of Intracellular and Plasma Levels of Amino Acids

A study was conducted in which venous blood samples were obtained from each of 29 normal adults. Each sample was obtained, prepared and tested substantially as described above. The concentrations were expressed in nanomoles per ml of intracellular water. The intracellular concentrations of amino acids were compared to the concurrent plasma levels of the same amino acids. The concentrations of aspartic acid, glutamine, glutamic acid, serine, asparagine and glycine varied substantially, the differences ranging from about 400 nm/ml ICW (aspartic acid) to about 1300 nm/ml ICW (glutamine, serine and asparagine). The difference between intracellular and extracellular amino acid was at least significant in all but two amino acids, namely valine and citrulline.

A similar study was performed using 57 normal infants. In this study, the differences for arginine, glutamic acid, glycine and tyrosine ranged from about 700 nm/ml ICW to about 2000 nm/ml ICW. The difference was statistically significant as to all the amino acids except for phenylalanine, tyrosine and valine. Although the intracellular-plasma variance occurred to a different extent and was substantial in different amino acids in the infant than in adults, it is demonstrated that plasma levels of amino acids do not accurately reflect intracellular levels of the same amino acids. It is suggested that measurement of intracellular amino acids is required to accurately assess the amino acid substrate available at the cellular level for nutrient-dependent processes, such as protein synthesis.

2. Comparison of Rate at Which Intracellular Amino Acids and Plasma Amino Acids Respond to Therapy.

The intracellular and plasma levels of 18 amino acids in 13 uremic adults were measured at their first visit to a dialysis center. These values were expressed as percentages of a control value for each amino acid. The plasma levels of 9 of the 18 amino acids were equal to or greater than 100% of the control plasma value. The intracellular levels of 8 amino acids equaled or exceeded 100% of the control.

The uremic adults were tested again at their second dialysis treatment. A dramatic change in intracellular amino acid composition was demonstrated. The concentrations of some of the amino acids increased and some decreased. However, after treatment, the intracellular level of all but two, or 16, of the amino acids equaled or exceeded 100% of control. One of the two amino acids which were measured at less than 100% of control had at least increased since the first visit.

On the other hand, the plasma levels of amino acids in these uremic adults did not so dramatically reflect the effect of therapy. At the time of the second visit, only seven of the 18 amino acids equaled or exceeded 100% of control.

Based upon these results, it is concluded that intracellular amino acid imbalance is a better indicator of successful treatment than corresponding extracellular imbalance. The extracellular amino acid levels reflect recent amino acid intakes. The amino acid concentrations in the plasma (extracellular) is a combination of amino acids entering the plasma from various organs, such as the liver and muscle, and movement of other amino acids from the plasma into various organs, such as the liver or muscle.

3. Effect of Adjusted Amino Acid Levels on Cell Protein Synthesis

The rate of protein synthesis occurring in leukocytes of uremic patients at their first dialysis treatment was compared to their protein synthesis rate after about three months of dialysis therapy. A marked increase was demonstrated. From this, it was concluded that adjustment towards normal of intracellular amino acids was associated with increased protein synthesis and thus an improved nutritional status.

4. Determination of Primary Amino Acids

Protein synthesis and intracellular levels of 17 amino acids were measured in 29 normal adults. A multivariate statistical analysis was made (by computer) of the results. Based on the measured protein synthesis rate of 2585 pmoles/hr/mgDNA, a subset of intracellular amino acids was identified which best predicted ($R^2=0.54$) protein synthesis. The subset comprises methionine ($-154$), isoleucine ($+295$), leucine ($-80$), phenylalanine ($+147$) and histidine ($-268$). ($P-0.019$)

Similarly, a subset of six primary intracellular amino acids was identified for 54 neonates. The mean rate of protein synthesis was 4043 pmoles/hr/mgDNA. The subset comprised leucine (84.1), methionine ($-222.4$), tyrosine ($-39.2$), glycine ($+9.5$), alanine ($-33.0$) and taurine ($-0.5$). This subset accounted for a variance in protein synthesis ($R^2$) equal to 0.365 (p=0.001).

5. Determination of Secondary Amino Acids

A multivariate analysis of the 29 normal adults tested in Example Nos. 1 and 4 above demonstrated that the intracellular level of each of the primary amino acids was predominately controlled by a distinct subset of secondary amino acids in the plasma. The results are shown in Table A.

TABLE A

Relationship and Effect of Statistically Selected Secondary (Plasma) Amino Acids on Statistically Selected Primary (Intracellular) Amino Acids (A.A.) in 29 Normal Adults

| Primary A.A. | Secondary A.A. | $R^2$ | p |
|---|---|---|---|
| Isoleucine$_{IC}$ = | 11.6 − 0.09* (citrulline) + 0.09 (isoleucine) − 0.09 (histidine) | 0.61 | 0.0001 |
| Leucine$_{IC}$ = | 29.1 + 0.12 (threonine) − 0.27 (citrulline) − 0.06 (valine) − 0.39 (histidine) | 0.60 | 0.0001 |
| Methionine$_{IC}$ = | 4.6 + 0.03 (taurine) − 0.07 (citrulline) | 0.19 | 0.060 |
| Phenylalanine$_{IC}$ = | 6.3 + 0.72 (aspartic acid) − 0.05 (citrulline) + 0.32 (methionine) + 0.06 (tyrosine) − 0.19 (histidine) | 0.69 | 0.0001 |
| Histidine$_{IC}$ = | 6.3 − 0.04 (citrulline) − 0.02 (valine) − 0.08 (leucine) − 0.08 (phenylalanine) − 0.08 (ornithine) + 0.05 (arginine) | 0.75 | 0.0001 |

*Partial Regression Coefficients

A multivariate analysis of the six intracelluar primary amino acids and the plasma levels of amino acids as studied in 54 normal neonates demonstrated the resuls shown in Table B.

TABLE B

Relationship and Effect of Statistically Selected Secondary (Plasma) Amino Acids on Statistically Selected Primary (Intracellular) Amino Acids (A.A.) in 54 Normal Neonates

| Primary A.A. | Secondary A.A. | $R^2$ | p |
|---|---|---|---|
| Leucine | 0.5* (methionine) − 0.02 (phenylalanine) − 0.02 (arginine) − 0.7 (citrulline) + 0.02 (ornithine) + 0.2 (taurine) | 0.49 | 0.0001 |
| Methionine | − 0.08 (tryptophane) + 0.01 (histidine) − 0.06 (arginine) − 0.03 (glutamic) − 0.09 (citrulline) + 0.06 (taurine) | 0.44 | 0.0002 |
| Tyrosine | 0.08 (isoleucine) + 0.03 (lysine) + 0.1 (histidine) − 0.1 (arginine) − 0.05 (glutamic) − 0.2 (citrulline) | 0.45 | 0.0001 |
| Taurine | 10.3 (isoleucine) + 13.3 (lysine) − 18.6 (histidine) − 8.1 (arginine) − 39.6 (aspartic acid) + 2.6 (glycine) | 0.45 | 0.0001 |
| Glycine | − 1.9 (valine) + 4.3 (methionine) + 2.7 (lysine) − 4.0 (histidine) + 1.0 (tyrosine) + 1.9 (taurine) | 0.39 | 0.001 |
| Alanine | 1.0 (methionine − 1.1 (phenylalanine) + 0.3 (lysine) + 0.2 (glutamic) − 1.6 (citrulline) + 0.5 (taurine) | 0.38 | 0.001 |

*Partial Regression Coefficients

Based on the data in Tables A and B it was concluded that a subject having an abnormal level of a selected primary amino acid may be successfully treated by administration of an amino acid solution comprising the amino acids identified as secondary to the abnormal primary amino acid. Adjustment of the amino acids comprising the secondary set could either increase or decrease the abnormal level of the primary amino acid, as needed. This restores the balance within the set of primary amino acids.

Based on the foregoing, it is apparent that the method of the present invention makes possible an accurate and current assessment of the nutritional status of a subject. Further, the present invention makes possible treatment of nutritional disorders by administration of a nutrient composition comprising those nutrients specifically required for improved metabolic function. Such therapy minimizes exposure of the subject of unneeded exogenous and potentially detrimental substances and also minimizes expense of nutritional therapy.

Changes may be made in the nature, composition, operation and arrangement of the various elements, steps and procedures described herein without departing from the spirit and scope of the invention as defined in the following claims.

What is claimed:

1. A method for assessing nutritional status in a subject, comprising:
   measuring the rate of at least one selected intracellular metabolic process;
   measuring the intracellular levels of selected amino acids;
   for each selected intracellular metabolic process, identifying the primary intracellular amino acids; and
   identifying each of the primary intracellular amino acids which is present at an abnormal level.

2. The method of claim 1 wherein protien synthesis is measured as one of the selected intracellular metabolic processes.

3. The method of claim 2 wherein glucose metabolism and energy production are also measured as selected intracellular metabolic processes.

4. The method of claim 1 wherein energy production is measured as one of the selected intracellular metabolic processes.

5. The method of claim 1 wherein glucose metabolism is measured as one of the selected intracellular metabloic processes.

6. The method of claim 1 wherein the measuring of the selected intracellular amino acids and the selected intracellular mteabolic process are carried out on leukocytes obtained from a sample of the subject's blood.

7. The method of claim 6 in which all the measurements are made on leukocytes obtained from a single blood sample.

8. The method of claim 1 wherein multivariate statistical analysis is used to identify the normal primary amino acids in a selected population.

9. The method of claim 1 further comprising:
measuring at least one non-amino acid intracellular nutrient.

10. The method of claim 9 wherein all the measurements are carried out on leukocytes from a single blood sample.

11. A method for treating a subject for a nutritional disorder, comprising:
measuring the intracellular levels of selected amino acids;
measuring the rate of at least one selected intracellular metabolic process;
for each selected intracellular metabolic process, identifying the primary intracellular amino acids;
identifying wach of the primary intracellular amino acids which is present at an abnormal level;
for each primary intracellular amino acid present at an abnormal level, identifying a set of secondary extracellular amino acids; and
administering to the subject an effective amount of a nutrient composition comprising the identified secondary amino acids in normal extracellular concentrations.

12. The method of claim 11 wherein the nutrient composition further comprises the indentified primary amino acids present intracellularly at below normal levels.

13. The method of claim 12 wherein glucose metabolism and energy production are also measured as selected intracellular metabolic processes.

14. The method of claim 12 wherein all the measurements are carried out on leukocytes from a single blood sample.

15. The method of claim 11 wherein the selected metabolic process is protein synthesis.

16. The method of claim 11 wherein the measurements of the selected intracellular amino acids and the selected intracellular metabolic process are carried out on leukocytes obtained from a sample of plasma.

17. The method of claim 16 in which all the measurements are made on leukocytes obtained from a single blood sample.

18. The method of claim 11 wherein multivariate statistical analysis is used to identify the normal primary and secondary amino acids in a selected population.

19. The method of claim 11 wherein energy production is measured as one of the selected intracellular metabolic processes.

20. The method of claim 11 in which glucose metabolism is measured as one of the selected intracellular metabolic processes.

21. The method of claim 11 further comprising: measuring at least one non-amino acid intracellular nutrient.

22. The method of claim 11 wherein multiple doses are administred to the subject, and wherein the rate of the selected metabolic process is repeatedly measured, and wherein the administration of the doses continues at least until the rate of the selected metabolic process approaches normal.

23. A method for treating a subject for a nutritional disorder, comprising:
administering to the subject an effective amount of a nutrient composition comprising normal plasma concentrations of selected secondary amino acids, wherein the secondary amino acids were selected by:
measuring the intracellular levels of selected amino acids;
measuring the rate of at least one selected intracellular metabolic process;
for each selected intracellular metabolic proscess, identifying the primary intracellular amino acids;
identifying each of the primary intracellular amino acids which is present at an abnormal level;
for each primary intracellular amino acid present at an abnormal level, identifying a set of secondary amino acids; and
administering to the subject an effective amount of a nutrient composition comprising the identified secondary amino acids in normal extracellular concentrations.

24. The method of claim 23 wherein the nutrient composition further comprises the identified primary amino acids present intracellularly at below normal levels.

25. The method of claim 24 wherein all the measurements are carried out on leukocytes from a single blood sample.

26. The method of claim 23 wherein the selected metabolic process is protein synthesis.

27. The method of claim 23 wherein the measurements of the selected intracellular amino acids and the selected intracellular metabolic process are carried out on leukocytes obtained from a sample of blood.

28. The method of claim 27 in which all the measurements are made on leukocytes obtained from a single blood sample.

29. The emthod of claim 23 wherein multivariate statistical analysis is used to identify the normal primary and secondary amino acids in a selected population.

30. The method of claim 29 wherein glucose metabolism and energy production are also measured as selected intracellular metabolic processes.

31. The method of claim 27 wherein energy production is measured as one of the selected intracellular metabolic processes.

32. The method of claim 31 further comprising:
measuring at least one non-amino acid intracellular nutrient.

33. The method of claim 23 wherein multiple doses are administered to the subject, and wherein the rate of the selected metabloic process is repeatedly measured, and wherein the administration of the doses continues at least until the rate of the selected metabolic process approaches normal.

34. The method of claim 23 in which glucose metabolism is measured as one of the selected intracellular metabolic processes.

* * * * *

UNITED STATES PATENT AND TRADEMARK OFFICE
CERTIFICATE OF CORRECTION

PATENT NO. : 4,818,516
DATED : April 4, 1989
INVENTOR(S) : Jack Metcoff

It is certified that error appears in the above—identified patent and that said Letters Patent is hereby corrected as shown below:

On the title page;

Page 1, under "Other Publications", col. 2, line 25, please delete "Insolation" and substitute therefor --Isolation--.

UNITED STATES PATENT AND TRADEMARK OFFICE
CERTIFICATE OF CORRECTION

PATENT NO. : 4,818,516
DATED : April 4, 1989
INVENTOR(S) : Jack Metcoff

It is certified that error appears in the above—identified patent and that said Letters Patent is hereby corrected as shown below:

Col. 1, line 6, please insert as the first sentence --This invention was made with Government support. The Government has certain rights in this invention.--

Col. 2, line 45, please delete the sentence "A preferred vessel is a blood collection tube, such as a red stoppered Vacutainer No. 6432 (125 mm length) or a red stoppered Veniject No. KT-200 (100 mm length)." and substitute therefor --A preferred vessel is a 15 ml plastic conical centrifuge tube.--

Col. 2, line 51, please delete the word "molucular" and substitute therefor --molecular--.

Col. 3, line 19, please delete "1.5 ml" and substitute therefor --15 ml--.

Col. 3, line 56, please delete the numeral "7.0" and substitute therefor the numeral --7.4--.

UNITED STATES PATENT AND TRADEMARK OFFICE
CERTIFICATE OF CORRECTION

PATENT NO. : 4,818,516
DATED : April 4, 1989
INVENTOR(S) : Jack Metcoff

It is certified that error appears in the above—identified patent and that said Letters Patent is hereby corrected as shown below:

Col. 3, lines 56 through 58, please delete ", CAP type II or better, 3.5 sodium chloride (w/v) solution and 0.16M potassium chloride".

Col. 5, line 55, following "0.25", please insert --$\mu$--.

Col. 7, line 1, please delete the word "fitered" and substitute therefor --filtered--.

Col. 7, line 10, please delete the word "incubted" and substitute therefor --incubated--.

Col. 7, line 59, please delete "Of" and substitute therefor --of--.

Col. 8, line 2, please delete the word "bbove" and substitute therefor --above--.

Col. 8, line 5, please delete "1:100" and substitute therefor --1:10--.

UNITED STATES PATENT AND TRADEMARK OFFICE
CERTIFICATE OF CORRECTION

PATENT NO. : 4,818,516
DATED : April 4, 1989
INVENTOR(S) : Jack Metcoff

It is certified that error appears in the above—identified patent and that said Letters Patent is hereby corrected as shown below:

Col. 8, line 50, please delete "Of" and substitute therefor --of--.

Col. 9, line 10, following "hr", please insert -- - -- and delete the word "of".

Col. 10, line 3, please delete the word "anayzed" and substitute therefor --analyzed--.

Col. 10, line 16, please delete the word "apargine" and substitute therefor --aspargine--.

Col. 10, line 22, immediately preceding the word "phenylalanine", please insert --to elute methionine, isoleucine and leucine. Then a third element is introduced to elute--.

Col. 10, line 24, please delete the word "tryptophane" and substitute therefor --tryptophan--.

Col. 10, line 61, please delete the word "one" and substitute therefor the word --the--.

UNITED STATES PATENT AND TRADEMARK OFFICE
CERTIFICATE OF CORRECTION

PATENT NO. : 4,818,516
DATED : April 4, 1989
INVENTOR(S) : Jack Metcoff

It is certified that error appears in the above—identified patent and that said Letters Patent is hereby corrected as shown below:

Col. 10, line 68, please delete the word "one" and substitute therefor --the--.

Col. 12, line 40, immediately following the word "measured", please insert --for a baseline--.

Col. 12, line 40, please delete "their first" and substitute therefor --a--.

Col. 12, line 41, please delete the word "a" and substitute therefor --the--.

Col. 12, line 44, please delete the word "greater" and substitute therefor --less--.

Col. 12, line 47, immediately preceding the word "uremic", please insert --same--.

Col. 12, line 47, please delete the words "at their second" and substitute therefor --after about two months of--.

UNITED STATES PATENT AND TRADEMARK OFFICE
CERTIFICATE OF CORRECTION

PATENT NO. : 4,818,516
DATED : April 4, 1989
INVENTOR(S) : Jack Metcoff

It is certified that error appears in the above—identified patent and that said Letters Patent is hereby corrected as shown below:

Col. 12, line 51, immediately following the word "after", please insert --about two months of--.

Col. 13, line 6, please delete "at their first dialysis treatment" and substitute therefor --after a few stabilizing dialysis treatments--.

Col. 13, line 22, immediately following "(P-0.019)", please insert --The numbers in parentheses are partial regression coefficients--.

Col. 13, line 34, please delete the words "controlled by" and substitute therefor --related to--.

Col. 13, line 59, please delete the word "resuls" and substitute therefor --results--.

Col. 14, line 63, please delete the word "protien" and substitute therefor --protein--.

Col. 15, line 6, please delete the word "metabloic" and substitute therefor --metabolic--.

UNITED STATES PATENT AND TRADEMARK OFFICE
CERTIFICATE OF CORRECTION

PATENT NO. : 4,818,516
DATED : April 4, 1989
INVENTOR(S) : Jack Metcoff

It is certified that error appears in the above—identified patent and that said Letters Patent is hereby corrected as shown below:

Col. 15, line 9, please delete the word "mteabolic" and substitute therefor --metabolic--.

Col. 15, line 15, immediately following the word "the", please insert --selected--.

Col. 15, line 31, please delete the word "wach" and substitute therefor --each--.

Col. 15, line 41, please delete the word "indentified" and substitute therefor --identified--.

Col. 16, line 4, please delete the word "administred" and substitute therefor --administered--.

Col. 16, line 19, please delete the word "proscess" and substitute therefor --process--.

Col. 16, line 22, immediately following the word "level;", please insert the word --and--.

UNITED STATES PATENT AND TRADEMARK OFFICE
CERTIFICATE OF CORRECTION

PATENT NO. : 4,818,516
DATED : April 4, 1989
INVENTOR(S) : Jack Metcoff

It is certified that error appears in the above—identified patent and that said Letters Patent is hereby corrected as shown below:

Col. 16, lines 25 through 29, please delete "; and administering to the subject an effective amount of a nutrient composition comprising the identified secondary amino acids in normal extracellular concentrations." and substitute therefor --identifying a set of secondary amino acids as found in normal subjects.--

Col. 16, line 46, please delete the word "emthod" and substitute therefor --method--.

Col. 16, line 49, please delete the numeral "29" and substitute therefor --24--.

Col. 16, line 52, please delete the numeral "27" and substitute therefor --23--.

UNITED STATES PATENT AND TRADEMARK OFFICE
CERTIFICATE OF CORRECTION

PATENT NO. : 4,818,516

DATED : April 4, 1989

INVENTOR(S) : Jack Metcoff

It is certified that error appears in the above-identified patent and that said Letters Patent is hereby corrected as shown below:

Col. 16, line 60, please delete the word "metabloic" and substitute therefor --metabolic--.

Signed and Sealed this

Nineteenth Day of June, 1990

Attest:

HARRY F. MANBECK, JR.

*Attesting Officer*   *Commissioner of Patents and Trademarks*